United States Patent [19]
Matsubara et al.

[11] Patent Number: 5,277,781
[45] Date of Patent: Jan. 11, 1994

[54] ZIRCONIA OXYGEN SENSOR

[75] Inventors: Shigeo Matsubara, Amagasaki; Toshiro Yamada, Kure; Yusuke Hirose, Sakai; Iwao Katayama, Takatsuki; Yukimi Miwa; Ryuji Tanoue, both of Amagasaki, all of Japan

[73] Assignee: Nisshin Steel Company Ltd., Tokyo, Japan

[21] Appl. No.: 716,777

[22] Filed: Jun. 18, 1991

[30] Foreign Application Priority Data

Jun. 25, 1990 [JP] Japan ............................ 2-166476
Apr. 26, 1991 [JP] Japan ............................ 3-122801

[51] Int. Cl.⁵ .......................................... G01N 27/26
[52] U.S. Cl. ................................ 204/421; 204/422; 204/423; 204/413
[58] Field of Search ................ 204/422, 421, 423, 413

[56] References Cited

U.S. PATENT DOCUMENTS

| | | | |
|---|---|---|---|
| 4,166,019 | 8/1979 | Roy et al. | 204/422 |
| 5,096,552 | 3/1992 | Fray | 204/421 |
| 5,112,456 | 5/1992 | Worrell et al. | 204/422 |

Primary Examiner—John Niebling
Assistant Examiner—Bruce F. Bell
Attorney, Agent, or Firm—Webb, Burden, Ziesenheim & Webb

[57] ABSTRACT

A zirconia oxygen sensor for measuring oxygen potential in the molten bath of a metal or alloy having a melting point of 350–550° C., which comprises a reference electrode which is of a substance having a melting point of the same level as or lower than the metal or alloy of which the oxygen potential is to be measured and being liquid at the measurement temperature and is open to the atmosphere, a vessel of a zirconia solid electrolyte containing 5–10% yttria or 10–20% of calcium oxide (CaO) and a lead wire which connects the reference electrode and said molten metal or alloy and its use are disclosed.

4 Claims, 2 Drawing Sheets

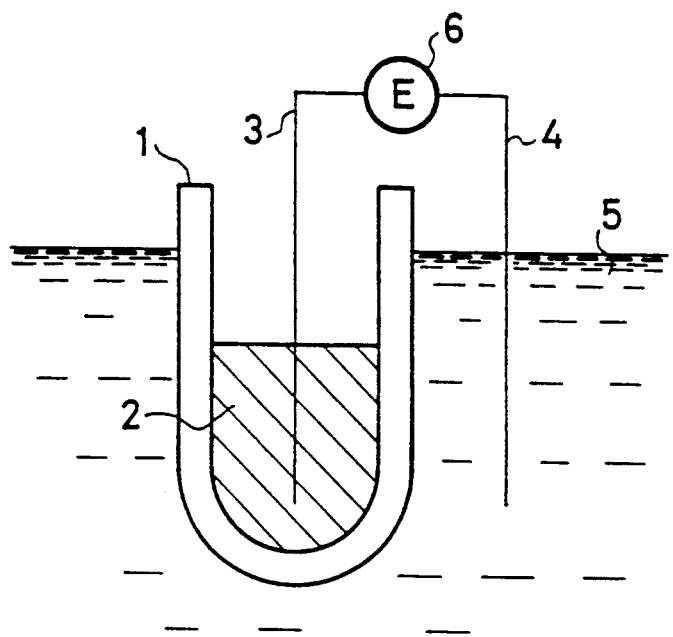

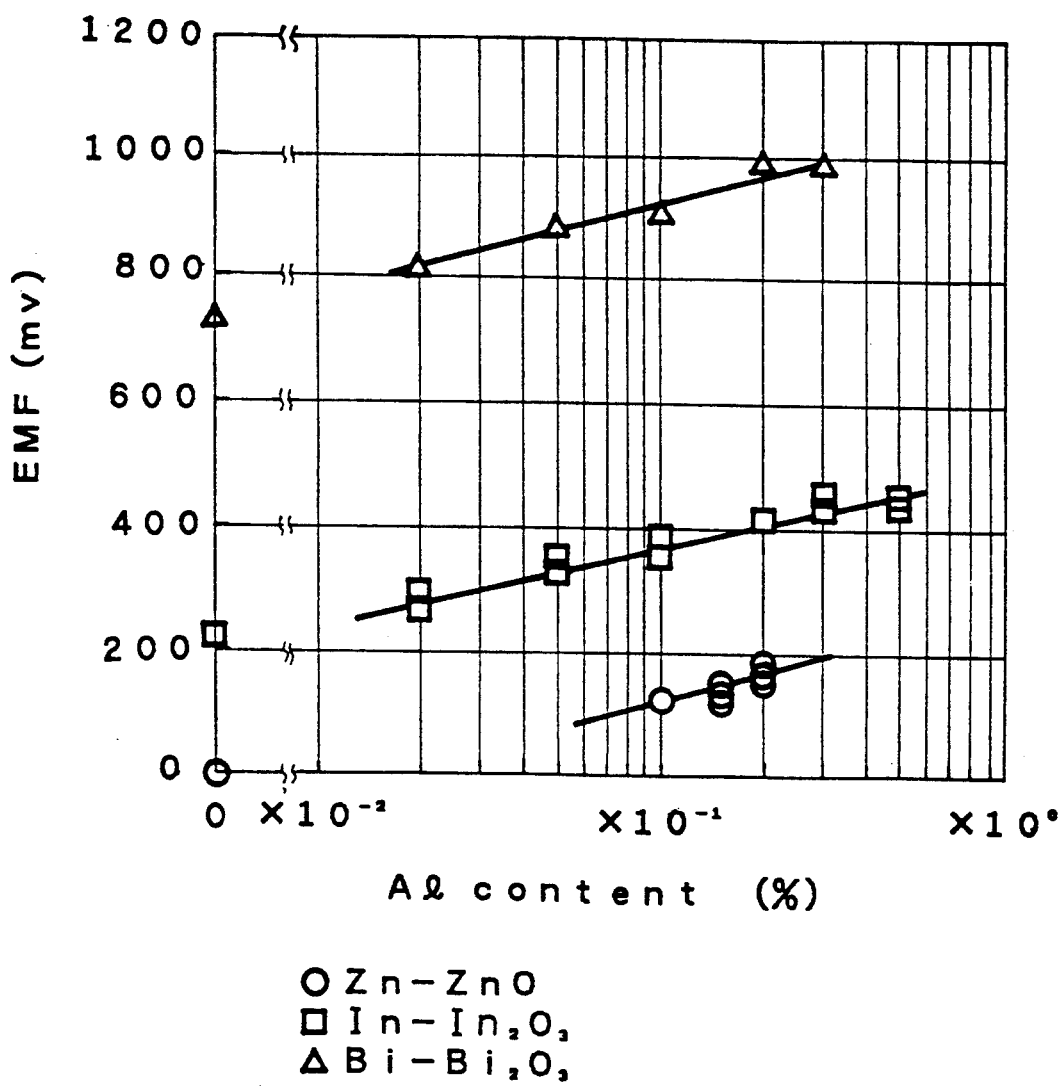

ZIRCONIA OXYGEN SENSOR

FIELD OF THE INVENTION

This invention relates to a zirconia oxygen sensor for measuring oxygen potential in low-melting metals and alloys.

BACKGROUND OF THE INVENTION

Recently varieties of metallic materials have come to be utilized and increasingly severe demands are being made regarding the quality of these materials. Thus control of the concentrations of impurities which have a close relation to the quality of the product is now considered to be of great significance in processing molten metal. Inter alia, the determination of oxygen potential in molten metal is very important in the control of the concentrations of oxygen and impurity elements which are in equilibrium with oxygen. A typical example is the determination of oxygen potential in molten steel and copper.

As a means for determining oxygen potential in molten steel and copper, zirconia oxygen sensor- is known, which utilizes the electromotive force of solid electrolyte. However, such an oxygen sensor can be used only in a rather high temperature range such as 1500–1800° C. for steel and 1000–1300° C. for copper.

It has been commonly accepted that the known zirconia oxygen sensor used for molten steel and copper cannot be used for determination of oxygen potential in a low-melting metal such as zinc, lead, bismuth, indium, gallium and alloys thereof whose melting point is not higher than 550° C. and there are hardly any reports of such measurement being conducted. It has been considered that the measurement of electromotive force itself is difficult at a low temperature such as 450–500° C., in molten zinc for instance, since the oxygen ion conductivity of the zirconia sensor is small at such a low temperature.

As an oxygen sensor for low-melting metals, an oxygen sensor, which utilizes thoria solid electrolyte and can be used in liquid sodium, is disclosed in Japanese Laid-Open Patent Publication No. 52-53494. However, thoria used in this sensor is a radioactive substance which is expensive and very difficult to handle and thus this sensor cannot easily be used in industry. That is to say, there has been known no oxygen sensor which can determine oxygen potential in low-melting metals.

As the reference electrode for a zirconia oxygen sensor, solid electrodes of Cr—$Cr_2O_3$ system, Mo—$MoO_2$ system, etc. are used for molten steel and those of Ni—NiO system, Fe—FeO system, etc. for molten copper. These electrodes exhibit rapid response to electromotive force at temperatures of 1000–1800° C. but they require an impracticably long time before the electromotive force stabilizes or otherwise the electromotive force does not stabilize when they are used in a low-melting metal which melts at a temperature of 350–550° C. We have now found that the oxygen potential in a low-melting metallic material can be measured by using a zirconia oxygen sensor comprising a reference electrode of a system consisting of a metal which has a melting point of the same level as or lower than that of the low-melting metal and is liquid at the measurement temperature and an oxide thereof, a zirconia solid electrolyte and a lead wire which connects the reference electrode and the molten low-melting metal.

DISCLOSURE OF THE INVENTION

This invention provides a zirconia oxygen sensor for measuring oxygen potential in the molten bath of a metal or alloy having a melting point of 350–550° C., which comprises a reference electrode which is of a system consisting of a metal having a melting point of the same level as or lower than the metal or alloy of which the oxygen potential is to be measured and being liquid at the measurement temperature and an oxide thereof dispersed therein and an oxide thereof and is open to the atmosphere, a vessel of a zirconia solid electrolyte and a lead wire which connects the reference electrode and said molten metal or alloy.

This zirconia oxygen sensor determines oxygen potential by measuring the electromotive force of an oxygen concentration cell composed of the reference electrode, the zirconia solid electrolyte, the molten metal and a lead wire.

The molten metals or alloys having melting points of 350–550° C., whose oxygen potential this invention intends to measure include zinc, lead, tin, bismuth, indium, gallium and alloys thereof.

In the present invention, the zirconia solid electrolyte acts as an oxygen ion conductor. When the zirconia solid electrolyte vessel containing the reference electrode material is brought into contact with a molten metal, an electromotive force is generated by virtue of the difference in the oxygen potentials. Examples of the zirconia solid electrolyte are zirconium oxide ($ZrO_2$) containing 5–10 mol % of yttrium oxide (yttria) ($Y_2O_3$) or 10–20 mol % calcium oxide (CaO), With pure $ZrO_2$, the oxygen concentration cell generates no electromotive force. With a yttria content of less than 5 mol %, the electromotive force does not stabilize and the cell response is slow. With more than 10 mol % yttria, the oxygen ion conductivity of the solid electrolyte is reduced. In both cases, the zirconia solid electrode is not usable. At temperatures lower than 350° C., the oxygen ion conductivity is very low and thus oxygen potential measurement is impossible. For molten steel and copper, zirconia solid electrolytes containing MgO or CaO are sometimes used, but these solid electrolytes do not generate sufficient electromotive force and the response is slow at temperatures lower than 550° C. Zirconia which contains metal oxide impurities represented by alumina in an amount of not more than 0.02 mass % is preferred because such zirconia exhibits a high oxygen ion conductivity, quick response and high stability.

Zirconia solid electrolyte per se is well known among those skilled in the art.

The reference electrode is composed of a metal having a melting point of the same level as or lower than the molten metal whose oxygen concentration is to be measured and fine particles of an oxide thereof dispersed therein. The electrode is liquid at the measurement temperature and exposed to the atmosphere. It is thought that the reference electrode is saturated with oxygen dissolved therein, wherefrom the oxygen potential is thermodynamically determined.

It is preferable to preheat the vessel of the zirconia solid electrolyte to a temperature near the melting point of the object molten metal. This is desirable because it brings the reference electrode to the measurement condition, which quickens the response and enhance the stability of the electrode in the measurement and also moderates the thermal shock when the solid electrolyte vessel is immersed into the molten metal.

Specific examples of the reference electrode are systems of In-In$_2$O$_3$, Pb-PbO, Sn-SnO$_2$, Bi-Bi$_2$O$_3$, Ga-Ga$_2$O$_3$ and Zn-ZnO, or systems of an alloy of each metal and its oxide. Of these, the melting point of Zn is 419.6° C. and, therefore, the electrode using the Zn—ZnO system cannot be used for metals having melting points lower than 419.6° C. However, the melting point of the reference electrode can be lowered by alloying.

Other systems are liquid in the temperature range of 350–550° C. and, accordingly, the zirconia solid oxygen sensor of the present invention is usable down to this temperature. The metal or alloy used in the reference electrode is liquid at the measuring temperature and has the metal oxide or oxides dispersed therein. Of the above-listed, In-In$_2$O$_3$, Bi-Bi$_2$O$_3$ and Zn-ZnO systems are preferred and of these In-In$_2$O$_3$ system is most preferred.

The material of the lead wire must not be reactable with or dissolvable in the reference electrode and the object molten metal. If the lead wire material reacts with or is dissolved in the molten metal or the reference electrode, various troubles occur. The oxygen potential of the reference electrode is varied and its electromotive force is affected impairing measurement accuracy and stability. If the lead wire metal is alloyed with the reference electrode and/or the molten metal, a new electromotive force is generated between the different alloys formed at the two ends of the lead wire in addition to the electromotive force generated by the oxygen potential difference and thus the correct electromotive force generated by the oxygen potential cannot be determined.

According to our experiments, C, W, Mo, Re, Ta, Ir, Os and stainless steels neither react with nor dissolve in the above-described low-melting metals and reference electrodes and are preferable as lead wire materials. Of these, W and Mo and stainless steels are easy to handle.

This invention enables determination of oxygen potential of low-melting metals and alloys.

An application of the zirconia oxygen sensor is determination of aluminum dissolved in a zinc plating bath. The zinc bath for the hot dip zinc plating (galvanizing) of steel sheets normally contains a small amount (up to around 0.2 mass %) of aluminum. For the quality control in a high speed hot-dip plating line, a rapid method for determining the aluminum content is required. Therefore, chemical analysis is no longer employed nowadays, having been replaced by fluorescence X-ray analysis. However, even this instrumental method takes a considerably long time and also what is determined by this method is the total aluminum when it is the amount of dissolved metallic aluminum only that has to be determined. We noted the fact that normally the zinc both is saturated with oxygen dissolved from the atmosphere and the normal oxygen content of a zinc bath is known but aluminum, which has a stronger affinity to oxygen, consumes oxygen and reduces the oxygen potential of the zinc bath. Therefore, the aluminum concentration of a zinc plating bath can be determined by determining the oxygen potential of the zinc plating bath and this can be very easily and rapidly effected by immersing the zirconia oxygen sensor of the present invention in the zinc plating bath.

Works for developing the present invention was, in fact, started with the aim of enabling determination of the aluminum content of zinc plating baths.

A characteristic of the zirconia oxygen sensor of the present invention is that its temperature-dependency in measurement is very small.

BRIEF DESCRIPTION OF THE ATTACHED DRAWINGS

FIG. 1 is a schematic representation of an example of the present invention, wherein zirconia solid electrolyte vessel 1, reference electrode 2, lead wire 3 (reference electrode side) and 4 (molten metal side), molten metal 5 and potentiometer 6 are shown. FIG. 2 shows the relation between the electromotive force (oxygen potential) and the aluminum concentration of a hot dip zinc plating bath.

SPECIFIC DESCRIPTION OF THE INVENTION

Now the invention will be illustrated by way of working examples.

Example 1

A zirconia oxygen sensor composed of a reference electrode 2, a lead wire 3 (reference side), a potentiometer 6 and a lead wire 4 (molten metal side) was immersed in a zinc bath and a lead bath and the electromotive force generated between the reference electrode and the molten metal by the difference in the oxygen potentials was measured at the temperatures indicated in Table 1. The zirconia solid electrolytes and reference electrode are indicated in Table 1. The results are also shown in Table 1.

Electromotive force varies from reference electrode to reference electrode and from molten metal to molten metal. But it was measured with good reproducibility.

Comparative Example 1

Using the zirconia oxygen sensors indicated in Table 2, the electromotive force generated by the difference in the oxygen potentials between the reference electrode and molten zinc and molten lead was measured at the temperatures indicated in Table 2. The results are shown in Table 2. Zirconia oxygen sensors using electrolytes which do not satisfy the requirements of the present invention did not develop stabilized electromotive force. Even the zirconia oxygen sensor of the present invention did not work at 330° C.

Example 2

The aluminum concentration in a hot dip zinc plating bath was determined using zirconia oxygen sensors in accordance with the present invention indicated in Table 3.

The oxygen potential of a zinc bath, which contained 0.12 mass % of aluminum was measured using these zirconia oxygen sensors in the manner as described above at the temperatures indicated in Table 3. The results are also shown in Table 3.

The measurements showed that temperature difference could be neglected in the temperature range of 450–470° C.

Table 3 indicates that the zirconia oxygen sensors of the present invention stabilized rapidly and thus were able to quickly determine oxygen potentials.

Information was separately compiled regarding the relationship between the oxygen potential (electromotive force) and the aluminum content of the hot dip zinc plating bath for individual reference electrodes. A few examples of the relationship at 460° C. are indicated in the form of a logarithmic diagram as shown in FIG. 2.

Therefore, the value of the measured electromotive force immediately gives the aluminum concentration.

The results are shown in Table 3. As seen in the table, the zirconia oxygen sensor of the present invention gave values very close to the known aluminum content.

Comparative Example 2

Using the zirconia oxygen sensors indicated in Table 3, the electromotive force between the reference electrode and the zinc plating bath was measured in the same manner as described above. The results are also shown in Table 3.

Zirconia oxygen sensors, which are composed of the same components as the oxygen sensors of the present invention but whose zirconia did not contain the defined amount of yttria, did not give good results. Needless to say, the other prior art zirconia oxygen sensors did not give good results.

TABLE 1

| Solid Elect'lyte | Ref. Electrode | Bath Temp. (°C.) | Molten Metal | EMF | |
|---|---|---|---|---|---|
| 8 mol % Y₂O₃—ZrO₂ | In—In₂O₃ | 450 | Zn | ○ | 247.8 |
| 8 mol % Y₂O₃—ZrO₂ | Zn—ZnO | 450 | Zn | ○ | 0.1 |
| 8 mol % Y₂O₃—ZrO₂ | In—In₂O₃ | 360 | Pb | ○ | −546.0 |
| 15 mol % CaO—ZrO₂ | In—In₂O₃ | 450 | Zn | ○ | 249.2 |

TABLE 2

| Solid Elect'lyte | Ref. Electrode | Bath Temp. (°C.) | Molten Metal | EMF | |
|---|---|---|---|---|---|
| 15 mol % MgO—ZrO₂ | In—In₂O₃ | 450 | Zn | X | — |
| 8 mol % Y₂O₃—ZrO₂ | Fe—FeO | 450 | Zn | X | — |
| 8 mol % Y₂O₃—ZrO₂ | In—In₂O₃ | 330 | Pb | X | — |

○ EMF stabilizes withiun 30 sec.
X EMF does not stabilize.

TABLE 3

| Solid Electrode | Ref. Electrode | Lead Wire | Bath Temp. (°C.) | EMF | | AL % |
|---|---|---|---|---|---|---|
| Examples | | | | | | |
| 8 mol % Y₂O₃—ZrO₂ | In—In₂O₃ | W | 470 | ○ | 385.6 | 0.121 |
| " | Zn—ZnO | " | " | ○ | 131.1 | −0.130 |
| " | Pb—PbO | " | " | ○ | — | — |
| " | Sn—SnO₂ | " | " | ○ | 450.3 | — |
| " | Bi—Bi₂O₃ | " | " | ○ | 933.3 | 0.110 |
| " | Ga—Ga₂O₃ | " | " | ○ | 92.6 | — |
| " | In—In₂O₃ | C | " | ○ | 388.4 | 0.127 |
| " | " | Mo | " | ○ | 384.2 | 0.118 |
| " | " | Re | " | ○ | 386.6 | 0.123 |
| " | " | W | 450 | ○ | 382.7 | 0.115 |
| " | " | " | 500 | ○ | 385.1 | 0.120 |
| 5 mol % Y₂O₃—ZrO₂ | " | " | 470 | ○ | 391.9 | 0.135 |
| 10 mol % Y₂O₃—ZrO₂ | " | " | " | ○ | 390.6 | 0.132 |
| 10 mol % CaO—ZrO₂ | " | " | " | ○ | — | — |
| 20 mol % CaO—ZrO₂ | " | " | " | ○ | — | — |
| Compara. Example | | | | | | |
| 4 mol % Y₂O₃—ZrO₂ | In—In₂O₃ | W | 470 | X | — | — |
| 11 mol % Y₂O₃—ZrO₂ | " | " | " | X | — | — |
| 9 mol % CaO—ZrO₂ | " | " | " | X | — | — |
| 21 mol % CaO—ZrO₂ | " | " | " | X | — | — |
| 8 mol % Y₂O₃—ZrO₂ | Cu—Cu₂O | " | " | Δ | — | — |
| " | Fe—FeO | " | 600 | Δ | — | — |
| " | " | " | 470 | X | — | — |

We claim:

1. A zirconia oxygen sensor for measuring oxygen potential at a measuring temperature in a molten bath of a metal or alloy having a melting point of 350-550° C., comprising:
    a reference electrode selected from the group consisting of In—In₂O₃, Pb—PbO, Sn—SnO₂, Bi—Bi₂O₃, Ga—Ga₂O₃, Zn—ZnO or a system of an alloy of each said metal and its oxide;
    a vessel of a zirconia solid electrolyte containing 5-10 mol % yttria or 10-20 mol % calcium oxide, said reference electrode contained in said vessel; and
    a lead wire connecting the reference electrode and said bath of molten metal or alloy;
    said reference electrode being liquid at said measuring temperatured and open to the atmosphere.

2. The zirconia oxygen sensor as claimed n claim 1, wherein the lead wire is made of a metal selected from the group consisting of C, W, Mo, Re, Ta, Ir, Os and stainless steels.

3. The zirconia oxygen sensor as claimed in claim 2, wherein the reference electrode is a system selected from the group consisting of In—In₂O₃, Bi—Bi₂O₃ and Zn—ZnO.

4. The zirconia oxygen sensor as claimed in claim 4, wherein the reference electrode is a system of In—In₂O₃.

* * * * *

UNITED STATES PATENT AND TRADEMARK OFFICE
CERTIFICATE OF CORRECTION

PATENT NO. : 5,277,781
DATED : January 11, 1994
INVENTOR(S) : Shigeo Matsubara, Toshiro Yamada, Yusuke Hirose, Iwao Katayama, Yukimi Miwa and Ryuji Tanoue It is certified that error appears in the above-indentified patent and that said Letters Patent is hereby corrected as shown below:

Column 1 Line 16 "alia ," should read --alia,--.

Column 1 Line 23 "sensor-" should read --sensor--.

Column 2 Line 65 "enhance" should read --enhances--.

Column 3 Line 66 "Works" should read --Work--.

Column 6 Line 8 "withiun" should read --within--.

Claim 1 Line 51 Column 6 "temperatured" should read --temperature--.

Claim 2 Line 52 Column 6 "n" should read --in--.

Claim 4 Line 60 Column 6 "4" should read --3--.

Signed and Sealed this

Seventh Day of June, 1994

Attest:

BRUCE LEHMAN

Attesting Officer

Commissioner of Patents and Trademarks